United States Patent [19]
Hsu et al.

[11] Patent Number: 6,008,328
[45] Date of Patent: Dec. 28, 1999

[54] METHOD FOR PURIFYING KERATINOCYTE GROWTH FACTORS

[75] Inventors: Eric W. Hsu; William C. Kenney; Tim Tressel, all of Thousand Oaks, Calif.

[73] Assignee: Amgen Inc., Thousand Oaks, Calif.

[21] Appl. No.: 08/487,830

[22] Filed: Jun. 7, 1995

Related U.S. Application Data

[63] Continuation-in-part of application No. 08/323,339, Oct. 13, 1994, abandoned.

[51] Int. Cl.$^6$ .............................. C07K 1/14; C07K 1/16; C07K 1/18; C07K 14/50
[52] U.S. Cl. .......................... 530/412; 530/399; 530/416; 530/417; 530/402
[58] Field of Search ..................................... 530/399, 357, 530/412, 416, 417, 402

[56] References Cited

U.S. PATENT DOCUMENTS 5,331,095  7/1994  Shadle et al. .
5,677,278  10/1997  Gospodarowicz et al. .

FOREIGN PATENT DOCUMENTS

WO 90/08771  8/1990  WIPO .
WO 95/01434  1/1995  WIPO .

OTHER PUBLICATIONS

Abraham et al., "Human basic fibroblast growth factor: nucleotide sequence and genomic organization", *The EMBO Journal*, 5(10):2523–2528 (1986).
Delli Bovi et al., "An Oncogene Isolated by Transfection of Kaposi's Sarcoma DNA Encodes a Growtb Factor That Is a Member of the FGF Family", *Cell*, 50:729–737 (1987).
Dickson and Peters, "Potential oncogene product related to growth factors", *Nature*, 326:833 (1987).
Finch et al., "Human KGF is FGF–Related with Properties of a Paracrine Effector of Epithelial Cell Growth", *Science*, 245:752–755 (1989).
Habazettl et al., "Structure of hisactophin is similar to interleukin–1β and fibroblast growth factor", *Nature*, 359:855–858 (1992).
Jaye et al., "Human Endothelial Cell Growth Factor: Cloning, Nucleotide Sequence, and Chromosome Localization", *Science*, 233:541–545 (1986).
Marics et al., "Characterization of the HST–related FGF.6 gene, a new member of the fibroblast growth factor gene family", *Oncogene*, 4:335–340 (1989).
Yan et al., "Sequence of Rat Keratinocyte Growth Factor (Heparin–Binding Growth Factor Type 7)", *In Vitro Cell. Dev. Biol.*,27A:437–438 (1991).
Yoshida et al., "Genomic sequence of hst, a transofrming gene encoding a protein homologous to fibroblast growth factors and the int–2 encoded protein", *Proc. Natl. Acad. Sci., USA*, 84:7305–7309 (1987).
Zhan et al., "The Human FGF–5 Onocogene Encodes a Novel Protein Related to Fibroblast Growth Factors", *Molecular and Cellular Biology*, 8(8):3487–3495 (1988).
Arakawa et al., Protein Engineering, 6(5):541–46 (1993).
Chiu et al., Biochem. Biophys., 269:75–85 (1989).
Suzuki et al., FEBS Letters, 328(1–2):17–20 (1993).
Arakawa et al., "Production and characterization of an analog of acidic fibroblast growth factor with enhanced stability and biological activity", *Protein Engineering*, 6(5):541–546 (1993).
Burgess and Maciag, "The Heparin–Binding (Fibroblast) Growth Factor Family of Proteins", *Annu. Rev. Biochem.*, 58:575–606 (1989).
Chiu et al., "Placental Keratinocyte Growth Factor: Partial Purification and Comparison with Epidermal Growth Factor", *Biochem. Biophys.*, 269:75–85 (1989).
Ron, et al., "Expression of Biologically Active Recombinant Keratinocyte Growth Factor", *The Journal of Biological Chemistry*, 268(4):2984–2988 (1993).
Rubin et al., "Purfication and characterization of a newly Identified growth factor specific for epithelial cells", *Proc. Natl. Acad. Sci. USA*, 86:802–806 (1989).
Suzuki et al., "Spleen–derived growth factor, SDGF–3, Is identified as keratinocyte growth factor (KGF)", *FEBS Letters*, 328(1–2):17–20 (1993).

*Primary Examiner*—John Ulm
*Assistant Examiner*—Christine Saoud
*Attorney, Agent, or Firm*—Steven M. Odre; Ron K. Levy; Thomas D. Zindrick

[57] ABSTRACT

The present invention concerns the purification of keratinocyte growth factors.

30 Claims, 15 Drawing Sheets

FIG.1A

```
 |---OLIGO#25-----|              |-------OLIGO#1---------|
5'CAATCTACAATTCACAGA 3'        5'CAATGACCTAGGAGTAACAATCAAC 3'
5'CAATCTACAATTCACAGATAGGAAGAGGTCAATGACCTAGGAGTAACAATCAACTCAAGA-
 ---------+---------+---------+---------+---------+---------+ 60

-TTCATTTTCATTATGTTATTCATGAACACCCGGAGCACTACACTATAATGCACAAATGGA-
 ---------+---------+---------+---------+---------+---------+ 120
                                                       M H K W I

-TACTGACATGGATCCTGCCAACTTTGCTCTACAGATCATGCTTTCACATTATCTGTCTAG-
 ---------+---------+---------+---------+---------+---------+ 180
   L  T  W  I  L  P  T  L  L  Y  R  S  C  F  H  I  I  C  L  V

-TGGGTACTATATCTTTAGCTTGCAATGACATGACTCCAGAGCAAATGGCTACAAATGTGA-
 ---------+---------+---------+---------+---------+---------+ 240
   G  T  I  S  L  A  C  N  D  M  T  P  E  Q  M  A  T  N  V  N

-ACTGTTCCAGCCCTGAGCGACACACAAGAAGTTATGATTACATGGAAGGAGGGGATATAA-
 ---------+---------+---------+---------+---------+---------+ 300
   C  S  S  P  E  R  H  T  R  S  Y  D  Y  M  E  G  G  D  I  R

-GAGTGAGAAGACTCTTCTGTCGAACACAGTGGTACCTGAGGATCGATAAAAGAGGCAAAG-
 ---------+---------+---------+---------+---------+---------+ 360
   V  R  R  L  F  C  R  T  Q  W  Y  L  R  I  D  K  R  G  K  V

-TAAAAGGGACCCAAGAGATGAAGAATAATTACAATATCATGGAAATCAGGACAGTGGCAG-
 ---------+---------+---------+---------+---------+---------+ 420
   K  G  T  Q  E  M  K  N  N  Y  N  I  M  E  I  R  T  V  A  V

-TTGGAATTGTGGCAATCAAAGGGGTGGAAAGTGAATTCTATCTTGCAATGAACAAGGAAG-
 ---------+---------+---------+---------+---------+---------+ 480
   G  I  V  A  I  K  G  V  E  S  E  F  Y  L  A  M  N  K  E  G

-GAAAACTCTATGCAAAGAAAGAATGCAATGAAGATTGTAACTTCAAAGAACTAATTCTGG-
 ---------+---------+---------+---------+---------+---------+ 540
   K  L  Y  A  K  K  E  C  N  E  D  C  N  F  K  E  L  I  L  E

-AAAACCATTACAACACATATGCATCAGCTAAATGGACACACAACGGAGGGGAAATGTTTG-
 ---------+---------+---------+---------+---------+---------+ 600
   N  H  Y  N  T  Y  A  S  A  K  W  T  H  N  G  G  E  M  F  V
```

FIG. 1B

```
-TTGCCTTAAATCAAAAGGGGATTCCTGTAAGAGGAAAAAAAACGAAGAAAGAACAAAAAA-
---------+---------+---------+---------+---------+---------+ 660
   A  L  N  Q  K  G  I  P  V  R  G  K  K  T  K  K  E  Q  K  T

-CAGCCCACTTTCTTCCTATGGCAATAACTTAATTGCATATGGTATATAAAGAACCCAGTT
---------+---------+---------+---------+---------+---------+ 720
   A  H  F  L  P  M  A  I  T  *
              3'GGATACCGTTATTGAATT 5'
                |----OLIGO#26----|

-CCAGCAGGGAGATTTCTTTAAGTGGACTGTTTTCTTTCTTCTCAAAATTTTCTTTCCTTT
---------+---------+---------+---------+---------+---------+ 780

-TATTTTTTAGTAATCAAGAAAGGCTGGAAAAACTACTGAAAAACTGATCAAGCTGGACTT
---------+---------+---------+---------+---------+---------+ 840
                                                   3'ACCTGAA-
                                                    |------

-GTGCATTTATGTTTGTTTTAAG 3'
---------+---------+--- 862
-CACGTAAATACAAACAAAA 5'
  ---OLIGO#2--------|
```

FIG.3

```
                ClaI         XbaI                NdeI
            5'-ATCGATTTGATTCTAGAAGGAGGAATAACATATGAAAAAG-
                                                  M  K  K

RSH signal sequence                    MluI
 -CGCGCACGTGCTATCGCCATTGCTGTGGCTCTGGCAGGTTTCGCAACTAGTGCACA-3'
   R  A  R  A  I  A  I  A  V  A  L  A  G  F  A  T  S  A  H  A -

MluI
5'CGCGTGCAATGACATGACTCCAGAGCAAATGGCTACAAATGTGAACTGTTCCAGCCCTGA-
  ---------+---------+---------+---------+---------+---------+ 60
  -  C  N  D  M  T  P  E  Q  M  A  T  N  V  N  C  S  S  P  E

-GCGACACACAAGAAGTTATGATTACATGGAAGGAGGGGATATAAGAGTGAGAAGACTCTT-
  ---------+---------+---------+---------+---------+---------+ 120
    R  H  T  R  S  Y  D  Y  M  E  G  G  D  I  R  V  R  R  L  F

KpnI         ClaI
 -CTGTCGAACACAGTGGTACCTGAGGATCGATAAAAGAGGCAAAGTAAAAGGGACCCAAGA-
  ---------+---------+---------+---------+---------+---------+ 180
    C  R  T  Q  W  Y  L  R  I  D  K  R  G  K  V  K  G  T  Q  E

-GATGAAGAATAATTACAATATCATGGAAATCAGGACAGTGGCAGTTGGAATTGTGGCAAT-
  ---------+---------+---------+---------+---------+---------+ 240
    M  K  N  N  Y  N  I  M  E  I  R  T  V  A  V  G  I  V  A  I

EcoRI
 -CAAAGGGGTGGAAAGTGAATTCTATCTTGCAATGAACAAGGAAGGAAAACTCTATGCAAA-
  ---------+---------+---------+---------+---------+---------+ 300
    K  G  V  E  S  E  F  Y  L  A  M  N  K  E  G  K  L  Y  A  K

BsmI
 -GAAAGAATGCAATGAAGATTGTAACTTCAAAGAACTAATTCTGGAAAACCATTACAACAC-
  ---------+---------+---------+---------+---------+---------+ 360
    K  E  C  N  E  D  C  N  F  K  E  L  I  L  E  N  H  Y  N  T

NdeI
 -ATATGCATCAGCTAAATGGACACACAACGGAGGGGAAATGTTTGTTGCCTTAAATCAAAA-
  ---------+---------+---------+---------+---------+---------+ 420
    Y  A  S  A  K  W  T  H  N  G  G  E  M  F  V  A  L  N  Q  K

-GGGGATTCCTGTAAGAGGAAAAAAAACGAAGAAAGAACAAAAAACAGCCCACTTTCTTCC-
  ---------+---------+---------+---------+---------+---------+ 480
    G  I  P  V  R  G  K  K  T  K  K  E  Q  K  T  A  H  F  L  P

BamHI
 -TATGGCAATAACTTAATAG 3'            -plasmid DNA
  ---------+---------+--- 503       -sequence
    M  A  I  T  *  *
```

FIG.4

```
NdeI
5'TATGTGCAATGACATGACTCCAGAGCAAATGGCTACAAATGTGAACTGTTCCAGCCCTGA-
   ---------+---------+---------+---------+---------+---------+ 60
    M  C  N  D  M  T  P  E  Q  M  A  T  N  V  N  C  S  S  P  E

-GCGACACACAAGAAGTTATGATTACATGGAAGGAGGGGATATAAGAGTGAGAAGACTCTT-
   ---------+---------+---------+---------+---------+---------+ 120
    R  H  T  R  S  Y  D  Y  M  E  G  G  D  I  R  V  R  R  L  F

KpnI        ClaI
-CTGTCGAACACAGTGGTACCTGAGGATCGATAAAAGAGGCAAAGTAAAAGGGACCCAAGA-
   ---------+---------+---------+---------+---------+---------+ 180
    C  R  T  Q  W  Y  L  R  I  D  K  R  G  K  V  K  G  T  Q  E

-GATGAAGAATAATTACAATATCATGGAAATCAGGACAGTGGCAGTTGGAATTGTGGCAAT-
   ---------+---------+---------+---------+---------+---------+ 240
    M  K  N  N  Y  N  I  M  E  I  R  T  V  A  V  G  I  V  A  I

EcoRI
-CAAAGGGGTGGAAAGTGAATTCTATCTTGCAATGAACAAGGAAGGAAAACTCTATGCAAA-
   ---------+---------+---------+---------+---------+---------+ 300
    K  G  V  E  S  E  F  Y  L  A  M  N  K  E  G  K  L  Y  A  K

BsmI
-GAAAGAATGCAATGAAGATTGTAACTTCAAAGAACTAATTCTGGAAAACCATTACAACAC-
   ---------+---------+---------+---------+---------+---------+ 360
    K  E  C  N  E  D  C  N  F  K  E  L  I  L  E  N  H  Y  N  T

NdeI
-ATATGCATCAGCTAAATGGACACACAACGGAGGGGAAATGTTTGTTGCCTTAAATCAAAA-
   ---------+---------+---------+---------+---------+---------+ 420
    Y  A  S  A  K  W  T  H  N  G  G  E  M  F  V  A  L  N  Q  K

-GGGGATTCCTGTAAGAGGAAAAAAAACGAAGAAAGAACAAAAAACAGCCCACTTTCTTCC-
   ---------+---------+---------+---------+---------+---------+ 480
    G  I  P  V  R  G  K  K  T  K  K  E  Q  K  T  A  H  F  L  P

BamHI
-TATGGCAATAACTTAATAG 3'
   ---------+---------+--- 503
    M  A  I  T  *
```

FIG.5

```
     KpnI
         |-----------OLIGO#6-----------------||------OLIGO#7---------
5'      CTGCGTATCGACAAACGCGGCAAAGTCAAGGGCACCCAAGAGATGAAAAACAACTACAAT-
3'CATGGACGCATAGCTGTTTGCGCCGTTTCAGTTCCCGTGGGTTCTCTACTTTTTGTTGATGTTA-
     |---------------OLIGO#9--------------------||--OLIGO#10--------
       - L  R  I  D  K  R  G  K  V  K  G  T  Q  E  M  K  N  N  Y  N -

EcoRI
     ---------------------||---------OLIGO#8-------------------|
5'-ATTATGGAAATCCGTACTGTTGCTGTTGGTATCGTTGCAATCAAAGGTGTTGAATCTG       3'
3'-TAATACCTTTAGGCATGACAACGACAACCATAGCAACGTTAGTTTCCACAACTTAGACTTAA  5'
     -------------------------||----OLIGO#11---------------------|
        I  M  E  I  R  T  V  A  V  G  I  V  A  I  K  G  V  E  S  E -
```

FIG.6

```
         XbaI
     |-----OLIGO#12-----|
5'AGTTTTGATCTAGAAGGAGG 3'
    |----------------------------OLIGO#14-----------------------
5'AGTTTTGATCTAGAAGGAGGAATAACATATGTGCAACGACATGACTCCGGAACAGATGGCT-

----------------------------||--------------OLIGO#15---------
-ACCAACGTTAACTGCTCCAGCCCGGAACGTCACACCCGTAGCTACGACTACATGGAAGTG-
                 3' GGGCCTTGCAGTGTGGGCAT 5'
                    |-----OLIGO#20-----|

---------------------OLIGO#15-----------------------------||-
-GTGACATCCGTGTTCGTCGTCTGTTCTGCCGTACCCAGTGGTACCTGCGTATCGACAAACG-
                                                3' ATAGCTGTTTGC-
                                                   |-OLIGO#21--

---------------------OLIGO#16-----------------------------
-TGGTAAAGTTAAAGGTACCCAGGAAATGAAAAACAACTACAACATCATGGAAATCCGTACT-
-ACCATTTC 5'
-------|

---------------------------||--------------OLIGO#17------------
-GTTGCTGTTGGTATCGTTGCAATCAAAGGTGTTGAATCTGAATTCTACCTGGCAATGAACA-
                 3' ACGTTAGTTTCCACAACTTA 5'
                    |-----OLIGO#22-----|

-----------------OLIGO#17--------------------------------||----
-AAGAAGGTAAACTGTACGCAAAAAAAGAATGCAACGAAGACTGCAACTTCAAAGAACTGAT-
                                              3'GAAGTTTCTTGACTA-
                                                |---OLIGO#23---

---------------------OLIGO#18-----------------------------
-CCTGGAAAACCACTACAACACCTACGCATCTGCTAAATGGACCCACAACGGTGGTGAAATG-
-GGACC 5'
-----|

-----------------------||------------------OLIGO#19---------
-TTCGTTGCTCTGAACCAGAAAGGTATCCCCGGTTCGTGGTAAAAAAACCAAAAAAGAACAGA-
                 3' GGTCTTTCCATAGGGCCAAG 5'
                    |-----OLIGO#24-----|

-------OLIGO#19------------------------------------|
-AAACCGCTCACTTCCTGCCGATGGCAATCACTTAATAGGATCCAGTTTTGA 3'
                                3' AATTATCCTAGGTCAAAACT 5'
                                   |----OLIGO#13------|
                                           BamHI
```

FIG. 7

```
5'ATGTCTAATGATATGACTCCGGAACAGATGGCTACCAACGTTAACTCCTCCTCCCCGGAA-
 ---------+---------+---------+---------+---------+---------+ 60
   M  S  N  D  M  T  P  E  Q  M  A  T  N  V  N  S  S  P  E

-CGTCACACGCGTTCCTACGACTACATGGAAGGTGGTGACATCCGCGTACGTCGTCTGTTC-
 ---------+---------+---------+---------+---------+---------+ 120
   R  H  T  R  S  Y  D  Y  M  E  G  G  D  I  R  V  R  R  L  F

-TGCCGTACCCAGTGGTACCTGCGTATCGACAAACGCGGCAAAGTCAAGGGCACCCAAGAG-
 ---------+---------+---------+---------+---------+---------+ 180
   C  R  T  Q  W  Y  L  R  I  D  K  R  G  K  V  K  G  T  Q  E

-ATGAAAAACAACTACAATATTATGGAAATCCGTACTGTTGCTGTTGGTATCGTTGCAATC-
 ---------+---------+---------+---------+---------+---------+ 240
   M  K  N  N  Y  N  I  M  E  I  R  T  V  A  V  G  I  V  A  I

-AAAGGTGTTGAATCTGAATTCTACCTGGCAATGAACAAAGAAGGTAAACTGTACGCAAAA-
 ---------+---------+---------+---------+---------+---------+ 300
   K  G  V  E  S  E  F  Y  L  A  M  N  K  E  G  K  L  Y  A  K

-AAAGAATGCAACGAAGACTGCAACTTCAAAGAACTGATCCTGGAAAACCACTACAACACC-
 ---------+---------+---------+---------+---------+---------+ 360
   K  E  C  N  E  D  C  N  F  K  E  L  I  L  E  N  H  Y  N  T

-TACGCATCTGCTAAATGGACCCACAACGGTGGTGAAATGTTCGTTGCTCTGAACCAGAAA-
 ---------+---------+---------+---------+---------+---------+ 420
   Y  A  S  A  K  W  T  H  N  G  G  E  M  F  V  A  L  N  Q  K

-GGTATCCCGGTTCGTGGTAAAAAAACCAAAAAAGAACAGAAAACCGCTCACTTCCTGCCG-
 ---------+---------+---------+---------+---------+---------+ 480
   G  I  P  V  R  G  K  K  T  K  K  E  Q  K  T  A  H  F  L  P

-ATGGCAATCACTTAA 3'
 ---------+----- 495
   M  A  I  T  *
```

FIG.8

```
5'ATGTGCAATGATATGACTCCTGAACAAATGGCTACCAATGTCAACTGTTCCTCTCCGGAG-
   ---------+---------+---------+---------+---------+---------+ 60
    M  C  N  D  M  T  P  E  Q  M  A  T  N  V  N  C  S  S  P  E

-CGCCACACCCGGAGTTACGATTACATGGAAGGTGGGGATATTCGCGTACGTCGTCTGTTC-
 ---------+---------+---------+---------+---------+---------+ 120
   R  H  T  R  S  Y  D  Y  M  E  G  G  D  I  R  V  R  R  L  F

-TGCCGTACCCAGTGGTACCTGCGTATCGACAAACGCGGCAAAGTCAAGGGCACCCAAGAG-
 ---------+---------+---------+---------+---------+---------+ 180
   C  R  T  Q  W  Y  L  R  I  D  K  R  G  K  V  K  G  T  Q  E

-ATGAAAAACAACTACAATATTATGGAAATCCGTACTGTTGCTGTTGGTATCGTTGCAATC-
 ---------+---------+---------+---------+---------+---------+ 240
   M  K  N  N  Y  N  I  M  E  I  R  T  V  A  V  G  I  V  A  I

-AAAGGTGTTGAATCTGAATTCTATCTTGCAATGAACAAGGAAGGAAAACTCTATGCAAAG-
 ---------+---------+---------+---------+---------+---------+ 300
   K  G  V  E  S  E  F  Y  L  A  M  N  K  E  G  K  L  Y  A  K

-AAAGAATGCAATGAAGATTGTAACTTCAAAGAACTAATTCTGGAAAACCATTACAACACA-
 ---------+---------+---------+---------+---------+---------+ 360
   K  E  C  N  E  D  C  N  F  K  E  L  I  L  E  N  H  Y  N  T

-TATGCATCTGCTAAATGGACCCACAACGGTGGTGAAATGTTCGTTGCTCTGAACCAGAAA-
 ---------+---------+---------+---------+---------+---------+ 420
   Y  A  S  A  K  W  T  H  N  G  G  E  M  F  V  A  L  N  Q  K

-GGTATCCCTGTTCAAGGTAAGAAAACCAAGAAAGAACAGAAAACCGCTCACTTCCTGCCG-
 ---------+---------+---------+---------+---------+---------+ 480
   G  I  P  V  Q  G  K  K  T  K  K  E  Q  K  T  A  H  F  L  P

-ATGGCAATCACTTAA 3'
 ---------+----- 495
   M  A  I  T  *
```

FIG. 9

```
5'ATGTCTAATGATATGACTCCGGAACAGATGGCTACCAACGTTAACTCCTCCTCCCCGGAA-
  ---------+---------+---------+---------+---------+---------+ 60
   M  S  N  D  M  T  P  E  Q  M  A  T  N  V  N  S  S  S  P  E

-CGTCACACGCGTTCCTACGACTACATGGAAGGTGGTGACATCCGCGTACGTCGTCTGTTC-
 ---------+---------+---------+---------+---------+---------+ 120
   R  H  T  R  S  Y  D  Y  M  E  G  G  D  I  R  V  R  R  L  F

-TGCCGTACCCAGTGGTACCTGCGTATCGACAAACGCGGCAAAGTCAAGGGCACCCAAGAG-
 ---------+---------+---------+---------+---------+---------+ 180
   C  R  T  Q  W  Y  L  R  I  D  K  R  G  K  V  K  G  T  Q  E

-ATGAAAAACAACTACAATATTATGGAAATCCGTACTGTTGCTGTTGGTATCGTTGCAATC-
 ---------+---------+---------+---------+---------+---------+ 240
   M  K  N  N  Y  N  I  M  E  I  R  T  V  A  V  G  I  V  A  I

-AAAGGTGTTGAATCTGAATTCTATCTTGCAATGAACAAGGAAGGAAAACTCTATGCAAAG-
 ---------+---------+---------+---------+---------+---------+ 300
   K  G  V  E  S  E  F  Y  L  A  M  N  K  E  G  K  L  Y  A  K

-AAAGAATGCAATGAAGATTGTAACTTCAAAGAACTAATTCTGGAAAACCATTACAACACA-
 ---------+---------+---------+---------+---------+---------+ 360
   K  E  C  N  E  D  C  N  F  K  E  L  I  L  E  N  H  Y  N  T

-TATGCATCTGCTAAATGGACCCACAACGGTGGTGAAATGTTCGTTGCTCTGAACCAGAAA-
 ---------+---------+---------+---------+---------+---------+ 420
   Y  A  S  A  K  W  T  H  N  G  G  E  M  F  V  A  L  N  Q  K

-GGTATCCCTGTTCAAGGTAAGAAAACCAAGAAAGAACAGAAAACCGCTCACTTCCTGCCG-
 ---------+---------+---------+---------+---------+---------+ 480
   G  I  P  V  Q  G  K  K  T  K  K  E  Q  K  T  A  H  F  L  P

-ATGGCAATCACTTAA 3'
 ---------+----- 495
   M  A  I  T  *
```

FIG.10

```
5' ATGTCTTCTCCTGAACGTCATACGCGTTCCTACGACTACATGGAAGGTGGTGACATCCGC-
   ---------+---------+---------+---------+---------+---------+ 60
    M  S  S  P  E  R  H  T  R  S  Y  D  Y  M  E  G  G  D  I  R

-GTACGTCGTCTGTTCTGCCGTACCCAGTGGTACCTGCGTATCGACAAACGCGGCAAAGTC-
   ---------+---------+---------+---------+---------+---------+ 120
    V  R  R  L  F  C  R  T  Q  W  Y  L  R  I  D  K  R  G  K  V

-AAGGGCACCCAAGAGATGAAAAACAACTACAATATTATGGAAATCCGTACTGTTGCTGTT-
   ---------+---------+---------+---------+---------+---------+ 180
    K  G  T  Q  E  M  K  N  N  Y  N  I  M  E  I  R  T  V  A  V

-GGTATCGTTGCAATCAAAGGTGTTGAATCTGAATTCTACCTGGCAATGAACAAAGAAGGT-
   ---------+---------+---------+---------+---------+---------+ 240
    G  I  V  A  I  K  G  V  E  S  E  F  Y  L  A  M  N  K  E  G

-AAACTGTACGCAAAAAAAGAATGCAACGAAGACTGCAACTTCAAAGAACTGATCCTGGAA-
   ---------+---------+---------+---------+---------+---------+ 300
    K  L  Y  A  K  K  E  C  N  E  D  C  N  F  K  E  L  I  L  E

-AACCACTACAACACCTACGCATCTGCTAAATGGACCCACAACGGTGGTGAAATGTTCGTT-
   ---------+---------+---------+---------+---------+---------+ 360
    N  H  Y  N  T  Y  A  S  A  K  W  T  H  N  G  G  E  M  F  V

-GCTCTGAACCAGAAAGGTATCCCGGTTCGTGGTAAAAAAACCAAAAAAGAACAGAAAACC-
   ---------+---------+---------+---------+---------+---------+ 420
    A  L  N  Q  K  G  I  P  V  R  G  K  K  T  K  K  E  Q  K  T

-GCTCACTTCCTGCCGATGGCAATCACTTAA 3'
   ---------+---------+---------+ 450
    A  H  F  L  P  M  A  I  T  *
```

FIG.11

```
5'ATGTCCTACGACTACATGGAAGGTGGTGACATCCGCGTACGTCGTCTGTTCTGCCGTACC-
  ---------+---------+---------+---------+---------+---------+ 60
   M  S  Y  D  Y  M  E  G  G  D  I  R  V  R  R  L  F  C  R  T

-CAGTGGTACCTGCGTATCGACAAACGCGGCAAAGTCAAGGGCACCCAAGAGATGAAAAAC-
  ---------+---------+---------+---------+---------+---------+ 120
   Q  W  Y  L  R  I  D  K  R  G  K  V  K  G  T  Q  E  M  K  N

-AACTACAATATTATGGAAATCCGTACTGTTGCTGTTGGTATCGTTGCAATCAAAGGTGTT-
  ---------+---------+---------+---------+---------+---------+ 180
   N  Y  N  I  M  E  I  R  T  V  A  V  G  I  V  A  I  K  G  V

-GAATCTGAATTCTACCTGGCAATGAACAAAGAAGGTAAACTGTACGCAAAAAAAGAATGC-
  ---------+---------+---------+---------+---------+---------+ 240
   E  S  E  F  Y  L  A  M  N  K  E  G  K  L  Y  A  K  K  E  C

-AACGAAGACTGCAACTTCAAAGAACTGATCCTGGAAAACCACTACAACACCTACGCATCT-
  ---------+---------+---------+---------+---------+---------+ 300
   N  E  D  C  N  F  K  E  L  I  L  E  N  H  Y  N  T  Y  A  S

-GCTAAATGGACCCACAACGGTGGTGAAATGTTCGTTGCTCTGAACCAGAAAGGTATCCCG -
  ---------+---------+---------+---------+---------+---------+ 360
   A  K  W  T  H  N  G  G  E  M  F  V  A  L  N  Q  K  G  I  P

-GTTCGTGGTAAAAAAACCAAAAAAGAACAGAAAACCGCTCACTTCCTGCCGATGGCAATC-
  ---------+---------+---------+---------+---------+---------+ 420
   V  R  G  K  K  T  K  K  E  Q  K  T  A  H  F  L  P  M  A  I

-ACTTAA 3'
  ------ 426
   T  *
```

FIG. 12

```
5'ATGTCCTACGACTACATGGAAGGTGGTGACATCCGCGTACGTCGTCTGTTCTGCCGTACC-
   --------+---------+---------+---------+---------+---------+  60
   M  S  Y  D  Y  M  E  G  G  D  I  R  V  R  R  L  F  C  R  T

-CAGTGGTACCTGCGTATCGACAAACGCGGCAAAGTCAAGGGCACCCAAGAGATGAAAAAC-
   --------+---------+---------+---------+---------+---------+  120
   Q  W  Y  L  R  I  D  K  R  G  K  V  K  G  T  Q  E  M  K  N

-AACTACAATATTATGGAAATCCGTACTGTTGCTGTTGGTATCGTTGCAATCAAAGGTGTT-
   --------+---------+---------+---------+---------+---------+  180
   N  Y  N  I  M  E  I  R  T  V  A  V  G  I  V  A  I  K  G  V

-GAATCTGAATTCTATCTTGCAATGAACAAGGAAGGAAAACTCTATGCAAAGAAAGAATGC-
   --------+---------+---------+---------+---------+---------+  240
   E  S  E  F  Y  L  A  M  N  K  E  G  K  L  Y  A  K  K  E  C-

-AATGAAGATTGTAACTTCAAAGAACTAATTCTGGAAAACCATTACAACACATATGCATCT-
   --------+---------+---------+---------+---------+---------+  300
   N  E  D  C  N  F  K  E  L  I  L  E  N  H  Y  N  T  Y  A  S

-GCTAAATGGACCCACAACGGTGGTGAAATGTTCGTTGCTCTGAACCAGAAAGGTATCCCT-
   --------+---------+---------+---------+---------+---------+  360
   A  K  W  T  H  N  G  G  E  M  F  V  A  L  N  Q  K  G  I  P

-GTTCAAGGTAAGAAAACCAAGAAAGAACAGAAAACCGCTCACTTCCTGCCGATGGCAATC-
   --------+---------+---------+---------+---------+---------+  420
   V  Q  G  K  K  T  K  K  E  Q  K  T  A  H  F  L  P  M  A  I

-ACTTAA 3'
   ------  426
   T  *
```

METHOD FOR PURIFYING KERATINOCYTE GROWTH FACTORS

This application is a continuation-in-part of U.S. Ser. No. 08/323,339, filed Oct. 13, 1994, now abandoned.

FIELD OF THE INVENTION

The present invention relates to the field of protein purification. Specifically, the present invention relates to the field of purifying keratinocyte growth factors.

BACKGROUND OF THE INVENTION

Polypeptide growth factors are important mediators of intercellular communication (Rubin et al. (1989), *Proc. Natl. Acad. Sci. USA*, 86:802–806). These molecules are generally released by one cell type and act to influence proliferation of other cell types.

One family of growth factors is the fibroblast growth factors (FGF). There are currently eight known FGF family members which share a relatedness among primary structures: basic fibroblast growth factor, bFGF (Abraham et al. (1986), *EMBO J.*, 5:2523–2528); acidic fibroblast growth factor, aFGF (Jaye et al. (1986), *Science*, 233:541–545); int-2 gene product, int-2 (Dickson & Peters (1987), *Nature*, 326:833); hst/kFGF (Delli-Bovi et al. (1987), *Cell*, 50:729–737, and Yoshida et al. (1987), *Proc. Natl. Acad. Sci. USA*, 84:7305–7309); FGF-5 (Zhan et al. (1988), *Mol. Cell. Biol.*, 8:3487–3495); FGF-6 (Marics et al. (1989), *Oncogene*, 4:335–340); keratinocyte growth factor (Finch et al. (1989), *Science*, 24:752–755; Rubin et al. (1989), *Proc. Natl. Acad. Sci. USA*, 86:802–806; Ron et al. (1993), *The Journal of Biological Chemistry*, 268(4):2984–2988; and Yan et al. (1991), *In Vitro Cell. Dev. Biol.*, 27A:437–438); and hisactophilin (Habazzettl et al. (1992), *Nature*, 359:855–858).

Among the FGF family of proteins, keratinocyte growth factor (KGF) is a unique effector of non-fibroblast epithelial (particularly keratinocyte) cell proliferation derived from mesenchymal tissues. The term "native KGF" refers to a natural human (hKGF) or recombinant (rKGF) polypeptide (with or without a signal sequence) as depicted by the amino acid sequence presented in SEQ ID NO:2 or an allelic variant thereof. [Unless otherwise indicated, amino acid numbering for molecules described herein shall correspond to that presented for the mature form of the native molecule (i.e., minus the signal sequence), as depicted by amino acids 32 to 194 of SEQ ID NO:2, with the initial MET in each such sequence being considered residue number "0".]

Native KGF may be isolated from natural sources. For example, hKGF can be isolated from medium conditioned by an embryonic lung fibroblast cell line (Rubin et al. (1989), supra. Three chromatographic steps, namely heparin-Sepharose™ (Pharmacia, Piscataway, N.J.) affinity chromatography, HPLC gel filtration, and reverse-phase HPLC, were used to obtain a purified hKGF preparation. Approximately 6 mg of hKGF were recovered from 10 liters of conditioned medium. These chromatographic steps only recovered 0.8% total hKGF based upon a mitogenic activity assay. A further example teaches the use of another chromatographic step using heparin-Sepharose™ affinity and Mono-S™ ion-exchange chromatographys (Pharmacia, Piscataway, N.J.) for isolation of rKGF produced in bacteria (Ron et al. (1993), *Journal of Biological Chemistry*, 268:2984–2988).

The properties of keratinocyte growth factors suggest a potential for the application thereof as a drug for promoting specific stimulation of epithelial cell growth. It therefore would be desirable to develop a method or methods for obtaining relatively high levels of homogeneous keratinocyte growth factors to provide sufficient quantities of material for comprehensive in vitro and in vivo biological evaluation and for a potential therapeutic application.

It is the object of this invention to provide a novel method for the purification of keratinocyte growth factors.

SUMMARY OF THE INVENTION

The present invention is directed to a first method for purifying a keratinocyte growth factor (KGF), the method comprising:

a) obtaining a solution containing KGF;

b) binding KGF from the solution of part (a) to a cation exchange resin;

c) eluting KGF in an eluate solution from the cation exchange resin;

d) passing the eluate solution from part (c) through a molecular weight exclusion matrix; and e) recovering KGF from the molecular weight exclusion matrix.

The invention is further directed to a second method for purifying a keratinocyte growth factor (KGF), the method comprising:

a) obtaining a solution containing KGF;

b) binding KGF from the solution of part (a) to a cation exchange resin;

c) eluting KGF in an eluate solution from the cation exchange resin;

d) performing hydrophobic interaction chromatography on the eluate solution of part (c); and e) recovering KGF from the hydrophobic interaction chromatography step of part (d).

Generally, the cation exchange chromatography step of the first or second methods may be conducted with any suitable buffer (e.g., phosphate buffer saline, sodium acetate or tris-HCL) at a pH of preferably between about 6.8–7.5. Suitable columns for use in this step include carboxymethyl cellulose, carboxymethyl agarose and sulfated agarose and cellulose columns (e.g.,columns of S-Sepharose Fast Flow™ resin, Mono-S™ resin and CM-cellulose™ resin, commercially available from Pharmacia, Piscataway, N.J.). The flow rate will be variable depending upon the column size.

The gel filtration step of the first method may be conducted in any suitable buffer (e.g., phosphate buffer saline) at a pH of preferably between about 7.0 and 7.5. Suitable columns for use in this step include agarose-based, acrylamide-based, silica-based or polymer-based size-exclusion columns (e.g., columns of Sephadex G-75™ resin and Superdex-75™ resin, commercially available from Pharmacia).

In a particularly preferred embodiment of the second method, free sulfhydryl groups may be oxidized prior to the hydrophobic interaction step, discussed below. Any manner of oxidation may be employed. For example, the protein may be exposed to atmospheric oxygen for a suitable period of time. Alternatively, various oxidation procedures may be employed. One such procedure is particularly suited for keratinocyte growth factors wherein one or more cysteine residues, as compared to the native KGF molecule, are deleted or replaced. In this procedure an oxidizing agent (e.g., cystamine dihydrochloride or another appropriate oxidizing agent, for instance, cystine, oxidized glutathione or divalent copper) may be added to a final concentration, adjusting the pH to preferably between about 7–9.5, with pH 9.0±0.3 being more preferred when using cystamine dihydrochloride), and holding the temperature at preferably between about 10–30° C., for an appropriate period. The second procedure may be used for oxidizing native KGF and other keratinocyte growth factors with comparable patterns of cysteine residues. In this procedure, oxidation may be accomplished by adding an appropriate amount of an ionic strength modifier (e.g., $(NH_4)_2SO_4$)), adjusting the pH to preferably between about 7.5–9.5, and holding the temperature at preferably between about 23±5° C. for an appropriate period.

The hydrophobic interaction step of the second method may be conducted by using any suitable buffer (e.g., sodium phosphate) at a pH of preferably between about 6.0–8.0, more preferably about 7.0, and by eluting with a decreasing linear $(NH_4)2SO_4$ gradient ranging from 2–0 M. Suitable columns for use in this step include alkyl or phenyl substituted resins (e.g., a column of Butyl-650M Toyopearl™ resin, commercially available from Tosohaas, Inc., Montgomeryville, Pa. and columns of phenyl Sepharose™ resin and phenyl Superose™ resin, commercially available from Pharmacia).

The process of the present invention may be used to purify KGF. For purposes of this invention, the term "KGF" includes native KGF, and KGF analog proteins characterized by a peptide sequence substantially the same as the peptide sequence of native KGF and which retain some or all of the biological activity of native KGF, particularly non-fibroblast epithelial cell proliferation. By "characterized by a peptide sequence substantially the same as the peptide sequence of native KGF" is meant a peptide sequence which is encoded by a DNA sequence capable of hybridizing to nucleotides 201 to 684 of SEQ ID NO:1, preferably under stringent hybridization conditions. Stringent conditions, in referring to homology in the hybridization context, will be stringent combined conditions of salt, temperature, organic solvents, and other parameters typically controlled in hybridization reactions. Exemplary stringent hybridization conditions are hybridization in 4 X SSC at 62–67° C., followed by washing in 0.1 X SSC 5 at 62–67° C. for approximately an hour. Alternatively, exemplary stringent hybridization conditions are hybridization in 45–55% formamide, 4 X SSC at 40–45° C. [See, T. Maniatis et. al., *Molecular Cloning* (A Laboratory Manual), Cold Spring Harbor Laboratory (1982), pages 387 to 389].

Thus, the proteins include allelic variations, or deletion (s), substitution(s) or insertion(s) of amino acids, including fragments, chimeric or hybrid molecules of native KGF. Examples of such proteins are taught in commonly owned U.S. Ser. No. 08/487.828 filed on the same date herewith now abandoned, (having a priority date of Oct. 13, 1994), U.S. Ser. No. 08/323,337, filed on Oct. 13, 1994 now abandoned, and U.S. Ser. No. 08/323,473, filed on Oct. 13, 1994 now abandoned. Generally, U.S. Ser. No. 08/487,828 teaches the modification of a keratinocyte growth factor having residues corresponding to $Cys^1$ and $Cys^{15}$ of native KGF (residues 32 and 46 of SEQ ID NO:2) by replacing or deleting such residues, with the resultant molecule having improved stability. U.S. Ser. No. 08/323,337 teaches the charge-change modification of a putative destabilizing cluster of basic residues within a keratinocyte growth factor having charge-change modifications of basic residues within a putative destabilizing cluster of basic residues within amino acid residues 41–153 of native KGF (amino acids 72–184 of SEQ ID NO:2), including charge-change modifications of amino acid residues $Arg^{41}$, $Gln^{43}$, $Lys^{95}$, $Asn^{137}$, $Gln^{138}$, $Lys^{139}$, $Arg^{144}$, $Lys^{147}$, $Gln^{152}$ and $Lys^{153}$ (amino acids 72 to 184 of SEQ ID NO:2). U.S. Ser. No. 08/323,473, filed on Oct. 13, 1994, teaches the modification of a keratinocyte growth factor having residues corresponding to a loop-forming region of $Asn^{115}$-$His^{116}$-$Tyr^{117}$-$Asn^{118}$-$Thr^{119}$ of KGF (amino acids 146–150 of SEQ ID NO:2) by substituting at least one amino acid having a higher loop-forming potential for an amino acid having a lower loop-forming potential in the identified loop-forming region of the protein.

As those skilled in the art will also appreciate, a variety of host-vector systems may be utilized to express the KGF protein-coding sequence. These include but are not limited to eucaryotic cell systems such as mammalian cell systems infected with virus (e.g., vaccinia virus, adenovirus, etc.); insect cell systems infected with virus (e.g., baculovirus); microorganisms such as yeast-containing yeast vectors; or to procaryotic cell systems such as bacteria transformed with bacteriophage DNA, plasmid DNA, or cosmid DNA. The expression elements of these vectors vary in their strengths and specificities. Depending on the host-vector system utilized, any one of a number of suitable transcription and translation elements may be used.

Once the protein product of KGF expression has been isolated, purified and assayed for KGF activity (using procedures known to those skilled in the art), it may be formulated in a variety of pharmaceutical compositions. Typically, such compositions include a suitable, usually chemically-defined, carrier or excipient for the therapeutic agent and, depending on the intended form of administration, other ingredients as well. The composition can include aqueous carriers or consist of solid phase formulations in which KGF is incorporated into non-aqueous carriers such as collagens, hyaluronic acid, and various polymers. The composition can be suitably formulated to be administered in a variety of ways, including by injection, orally, topically, intranasally and by pulmonary delivery.

BRIEF DESCRIPTION OF THE DRAWINGS

FIG. 1 shows the nucleotide (SEQ ID NO:1) and amino acid (SEQ ID NO:2) sequences of native KGF (the nucleotides encoding the mature form of native KGF is depicted by bases 201 to 684 of SEQ ID NO:1 and the mature form of KGF is depicted by amino acid residues 32 to 194 of SEQ ID NO:2).

FIG. 3 shows the nucleotide (SEQ ID NO:3) and amino acid (SEQ ID NO:4) sequences of the construct RSH-KGF.

FIG. 4 shows the nucleotide (SEQ ID NO:5) and amino acid (SEQ ID NO:6) sequences of the construct contained in plasmid KGF, wherein the initial methionine in the sequence should be considered residue number "0".

FIG. 5 shows the chemically synthesized OLIGOs (OLIGO#6 through OLIGO#11; SEQ ID NO:12–17, respectively) used to substitute the DNA sequence between a KpnI site and an EcoRI site for a KpnI site (from amino acid positions 46 to 85 of SEQ ID No:6) in the construct contained plasmid KGF to produce the construct in plasmid KGF(dsd).

FIG. 6 shows the chemically synthesized OLIGOs (OLIGO#12 through OLIGO#24; SEQ ID NO:18–30, respectively) used to construct KGF(codon optimized).

FIG. 7 shows the nucleotide (SEQ ID NO:31) and amino acid sequences (SEQ ID NO:32) of C(1,15)S, a KGF analog having substitutions of serine for cysteine at amino acid positions 1 and 15 of native KGF, wherein the initial methionine in the sequence should be considered residue number "0".

FIG. 8 shows the nucleotide (SEQ ID NO:33) and amino acid sequences (SEQ ID NO:34) of R(144)Q, a KGF analog having substitutions of serine for cysteine at amino acid positions 1 and 15 and a substitution of glutamic acid for arginine at amino acid position 144 of native KGF, wherein the initial methionine in the sequence should be considered residue number "0".

FIG. 9 shows the nucleotide (SEQ ID NO:35) and amino acid (SEQ ID NO:36) sequences of C(1,15)S/R(144)Q, a KGF analog having substitutions of serine for cysteine at amino acid positions 1 and 15 and a substitution of glutamine for arginine at amino acid position 144 of native KGF, wherein the initial methionine in the sequence should be considered residue number "0".

FIG. 10 shows the nucleotide (SEQ ID NO:37) and amino acid (SEQ ID NO:38) sequences of ΔN15, a KGF analog having a deletion of the first 15 amino acids of the N-terminus of native KGF, wherein the initial methionine in the sequence should be considered residue number "0".

FIG. 11 shows the nucleotide (SEQ ID NO:39) and amino acid (SEQ ID NO:40) sequences of ΔN23, a KGF analog having a deletion of the first 23 amino acids of the N-terminus of native KGF, wherein the initial methionine in the sequence should be considered residue number "0".

FIG. 12 shows the nucleotide (SEQ ID NO:41) and amino acid (SEQ ID NO:42) sequences of ΔN23/R(144)Q, a KGF analog having a deletion of the first 23 amino acids of the N-terminus and a substitution of glutamine for arginine at amino acid position 144 of native KGF, wherein the initial methionine in the sequence should be considered residue number "0".

DESCRIPTION OF SPECIFIC EMBODIMENTS

Figure 2A:
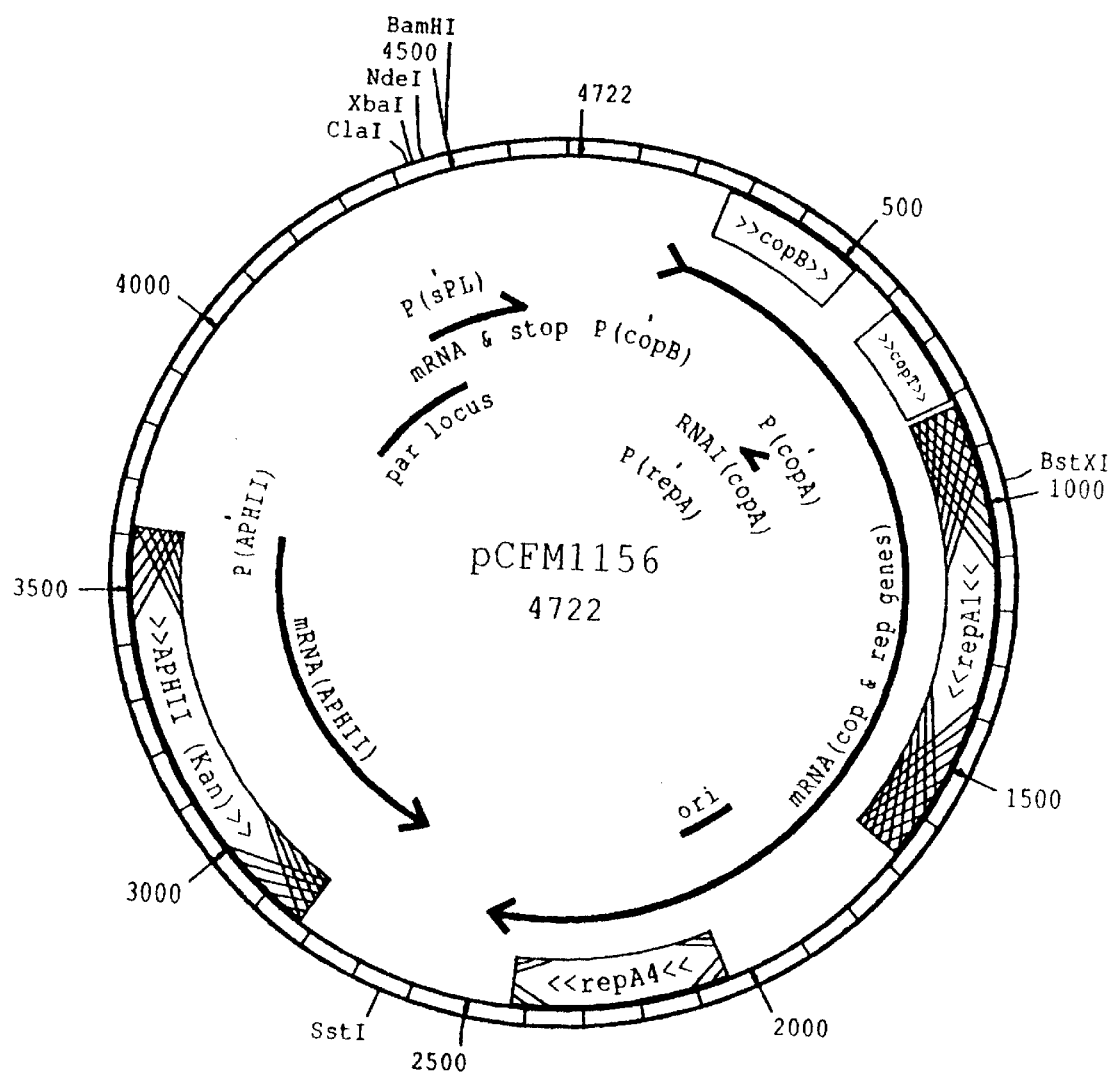
FIGS. 2A, 2B and 2C show the plasmid maps of pCFM1156, pCFM1656 and pCFM3102, respectively.

Standard methods for many of the procedures described in the following examples, or suitable alternative procedures, are provided in widely recognized manuals of molecular biology such as, for example, *Molecular Cloning*, Second Edition, Sambrook et al., Cold Spring Harbor Laboratory Press (1987) and *Current Protocols in Molecular Biology*, Ausabel et al., Greene Publishing Associates/Wiley-Interscience, New York (1990).

EXAMPLE 1

Preparation of DNA Coding for KGF and KGF Analogs

The cloning of the full-length human KGF gene (encoding a polypeptide with the sequence of native KGF) was carried out both by polymerase chain reaction (PCR) of RNA from an animal cell and by PCR of chemically synthesized (*E. coli* optimized codon) oligonucleotides ("OLIGOs"). Both procedures are described below:

PCR amplification using RNA isolated from cells known to produce the polypeptide was performed. Initially, cells from a human fibroblast cell line AG1523A (obtained from Human Genetic Mutant Cell Culture Repository Institute For Medical Research, Camden, N.J.) were disrupted with guanidium thiocyanate, followed by extraction (according to the method of Chomyzinski et al. (1987), *Anal. Biochem.*, 172:156). Using a standard reverse transcriptase protocol for total RNA, the KGF cDNA was generated. PCR (PCR#1) amplification of the KGF gene was carried out using the KGF CDNA as template and primers OLIGO#1 and OLIGO#2 that encode DNA sequences immediately 5' and 3' of the KGF gene [model 9600 Thermocycler (Perkin-Elmer Cetus, Norwalk, Conn.); 28 cycles; each cycle consisting of one minute at 94° C. for denaturation, two minutes at 60° C. for annealing, and three minutes at 72° C. for elongation]. A small aliquot of the PCR#1 product was then used as template for a second KGF PCR (PCR#2) amplification identical to the cycle conditions described above except for a 50° C. annealing temperature. For expression cloning of the KGF gene, nested PCR primers were used to create convenient restriction sites at both ends of the KGF gene. OLIGO#3 and OLIGO#4 were used to modify the KGF DNA product from PCR#2 to include MluI and BamHI restriction sites at the 5' and 3' ends of the gene, respectively [PCR#3; 30 cycles; each cycle consisting of one minute at 94° C. for denaturation, two minutes at 60° C. for annealing, and three minutes at 72° C. for elongation]. This DNA was subsequently cut with MluI and BamHI, phenol extracted and ethanol precipitated. It was then resuspended and ligated (using T4 ligase) into a pCFM1156 plasmid (FIG. 2A) that contained a "RSH" signal sequence to make construct RSH-KGF (FIG. 3). The ligation products were transformed (according to the method of Hanahan (1983), *J. Mol. Biol.*, 166:557) into *E. coli* strain FM5 (ATCC: 53911) and plated onto LB+kanamycin at 28° C. Several transformants were selected and grown in small liquid cultures containing 20 μg/mL kanamycin. The RSH-KGF plasmid was isolated from the cells of each culture and DNA sequenced. Because of an internal NdeI site in the KGF gene, it was not possible to directly clone the native gene sequence into the desired expression vector with the bracketed restriction sites of NdeI and BamHI. This was accomplished as a three-way ligation. Plasmid RSH-KGF was cut with the unique restriction sites of BsmI and SstI, and a ~3 kbp DNA fragment (containing the 3' end of the KGF gene) was isolated following electrophoresis through a 1% agarose gel. A PCR (PCR#4) was carried out as described for PCR#3 except for the substitution of OLIGO#5 for OLIGO#3. The PCR DNA product was then cut with NdeI and BsmI and a 311 bp DNA fragment was isolated following electrophoresis through a 4% agarose gel. The third fragment used in the ligation was a 1.8 kbp DNA fragment of pCFM1156 cut with NdeI and SstI isolated following electrophoresis through a 1% agarose gel. Following ligation (T4 ligase), transformation, kanamycin selection and DNA sequencing as described above, a clone was picked containing the construct in FIG. 4, and the plasmid designated KGF. Because of an internal ribosomal binding site that produced truncated products, the KGF DNA sequence between the unique KpnI and EcoRI sites was replaced with chemically synthesized OLIGOs (OLIGO#6 through OLIGO#11) to minimize the use of the internal start site (FIG. 5).

OLIGO#1 (SEQ ID NO:7): 5'-CAATGACCTAGG AGTAACAATCAAC-3'

OLIGO#2 (SEQ ID NO:8): 5'-AAAACAAAC ATAAATGCACAAGTCCA-3'

OLIGO#3 (SEQ ID NO:9): 5'-ACAACGCGT GCAATGACATGACTCCA-3'

OLIGO#4 (SEQ ID NO:10): 5'-ACAGGATCC TATTAAGTTATTGCCATAGGAA-3'

OLIGO#5 (SEQ ID NO:11): 5'-ACACATATGTGC AATGACATGACTCCA-3'

OLIGO#6 (SEQ ID NO:12): 5'-CTGCGTATCGAC AAACGCGGCAAAGTCAAGGGCACCC-3'

OLIGO#7 (SEQ ID NO:13): 5'-AAGAGATGAAAA
ACAACTACAATATTATGGAAATCCGTACTGTT-3'

OLIGO#8 (SEQ ID NO:14): 5'-GCTGTTGGTATC
GTTGCAATCAAAGGTGTTGAATCTG-3'

OLIGO#9 (SEQ ID NO:15): 5'-TCTTGGGTGCCCTTG
ACTTTGCCGCGTTTGTCGATACGCAGGTAC-3'

OLIGO#10 (SEQ ID NO:16): 5'-ACAGCAACAGTA
CGGATTTCCATAATATTGTAGTTGTTTTTCATC-3'

OLIGO#11 (SEQ ID NO:17): 5'-AATTCAGATTCA
ACACCTTTGATTGCAACGATACCA-3'

The OLIGOs were phosphorylated with T4 polynucleotide kinase and then heat denatured. The single-stranded (ss) OLIGOs were then allowed to form a ds DNA fragment by allowing the temperature to slowly decrease to room temperature. T4 ligase was then used to covalently link both the internal OLIGO sticky-ends and the whole ds OLIGO fragment to the KGF plasmid cut with KpnI and EcoRI. The new plasmid was designated KGF(dsd).

A completely *E. coli* codon-optimized KGF gene was constructed by PCR amplification of chemically synthesized OLIGOs #12 through 24.

utilized the outside primers (100 pmoles/100 μl rxn) OLIGO#12 and OLIGO#13 and 1 μl/100 μl rxn of a KGF template derived by ligation (by T4 ligase) of OLIGOs #14 through #19 (OLIGOs#15 through OLIGOs#18 were phosphorylated with T4 polynucleotide kinase) using OLIGOs#20 through OLIGOs#24 as band-aid oligos (Jayaraman et al. (1992), *Biotechniques*, 12:392) for the ligation. The final construct was designated KGF(codon optimized).

All of the KGF analogs described herein are composed in part from DNA sequences found in KGF(dsd) or KGF (codon optimized), or a combination of the two. The sequences are further modified by the insertion into convenient restrictions sites of DNA sequences that encode the particular KGF analog amino acids made utilizing one or more of the above-described techniques for DNA fragment synthesis. Any of the analogs can be generated in their entirety by either of the above described techniques. However, as a part of the general OLIGO design optimized *E. coli* codons were used where appropriate, although the presence of *E. coli* optimized codons in part or in toto of any of the genes where examined did not significantly increase

```
OLIGO#12 (SEQ ID NO:18):  5'-AGTTTTGATCTAGAAGGAGG-3'

OLIGO#13 (SEQ ID NO:19):  5'-TCAAAACTGGATCCTATTAA-3'

OLIGO#14 (SEQ ID NO:20):
        5'-AGTTTTGATCTAGAAGGAGGAATAACATATGTGCAACGACATGAC-
        TCCGGAACAGATGGCTACCAACGTTAACTGCTCCAGCCCGGAACGT-3'

OLIGO#15 (SEQ ID NO:21):
        5'-CACACCCGTAGCTACGACTACATGGAAGGTGGTGACATCCGTGTTC-
        GTCGTCTGTTCTGCCGTACCCAGTGGTACCTGCGTATCGACAAA-3'

OLIGO#16 (SEQ ID NO:22):
        5'-CGTGGTAAAGTTAAAGGTACCCAGGAAATGAAAAACAACTA-
        CAACATCATGGAAATCCGTACTGTTGCTGTTGGTATCGTTGCAATCAAA-3'

OLIGO#17 (SEQ ID NO:23):
        5'-GGTGTTGAATCTGAATTCTACCTGGCAATGAACAAAGAAGGTAAAC-
        TGTACGCAAAAAAAGAATGCAACGAAGACTGCAACTTCAAAGAA-3'

OLIGO#18 (SEQ ID NO:24):
        5'-CTGATCCTGGAAAACCACTACAACACCTACGCATCTGCTAAATGGA-
        CCCACAACGGTGGTGAAATGTTCGTTGCTCTGAACCAGAAAGGT-3'

OLIGO#19 (SEQ ID NO:25):
        5'-ATCCCGGTTCGTGGTAAAAAAACCAAAAAAGAACAGAAAACCGCT-
        CACTTCCTGCCGATGGCAATCACTTAATAGGATCCAGTTTTGA-3'

OLIGO#20 (SEQ ID NO:26):5'-TACGGGTGTGACGTTCCGGG-3'

OLIGO#21 (SEQ ID NO:27):5'-CTTTACCACGTTTGTCGATA-3'

OLIGO#22 (SEQ ID NO:28):5'-ATTCAACACCTTTGATTGCA-3'

OLIGO#23 (SEQ ID NO:29):5'-CCAGGATCAGTTCTTTGAAG-3'

OLIGO#24 (SEQ ID NO:30):5'-GAACCGGGATACCTTTCTGG-3'
```

OLIGOs #12 through 24 were designed so that the entire DNA sequence encoding native KGF was represented by OLIGOs from either the "Watson" or the "Crick" strand and upon PCR amplification would produce the desired double-stranded DNA sequence (FIG. 6) [PCR#5, Model 9600 thermocycler (Perkin-Elmer Cetus); 21 cycles, each cycle consisting of 31 seconds at 94° C. for denaturation, 31 seconds at 50° C. for annealing, and 31 seconds at 73° C. for elongation; following the 21 cycles the PCR was finished with a final elongation step of 7 minutes]. After PCR amplification, the DNA fragment was cut with XbaI and BamHI and the 521 bp fragment ligated into the expression plasmid pCFM1156 cut with the same enzymes. PCR#5 the yield of protein that could be obtained from cultured bacterial cells. FIGS. 7 to 12 set forth by convenient example particular KGF analog nucleotide and amino acid sequence constructions: C(1,15)S (FIG. 7); R(144)Q (FIG. 8); C(1,15)S/R(144)Q (FIG. 9); ΔN15 (FIG. 10); ΔN23 (FIG. 11) and ΔN23/R(144)Q (FIG. 12). All the KGF analog constructions described herein were DNA sequence confirmed.

Example 2

Purification from *E. coli*

Three different expression plasmids were utilized in the cloning of the KGF analog genes. They were pCFM1156

Figure 2B:
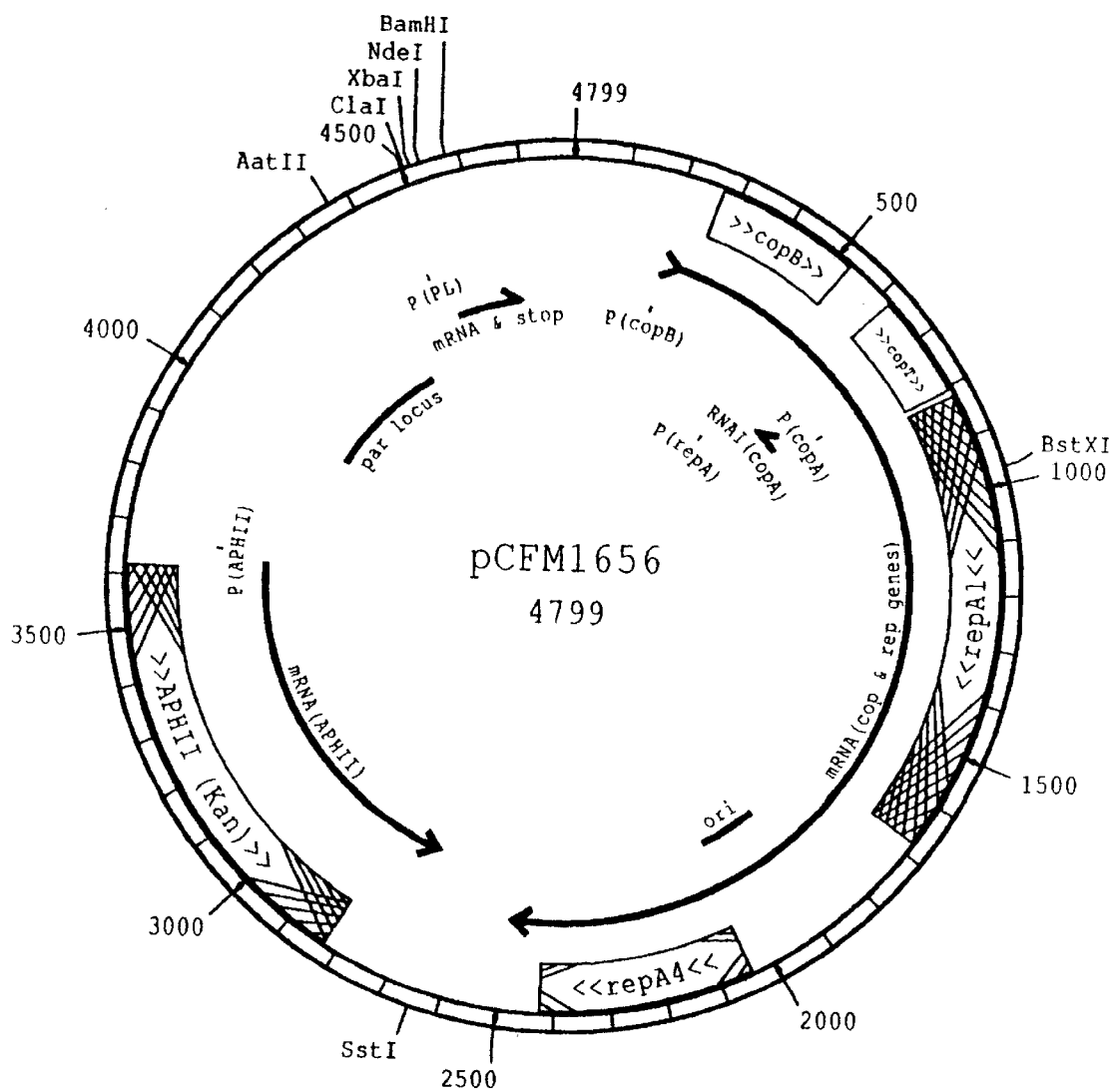
Figure 2C:
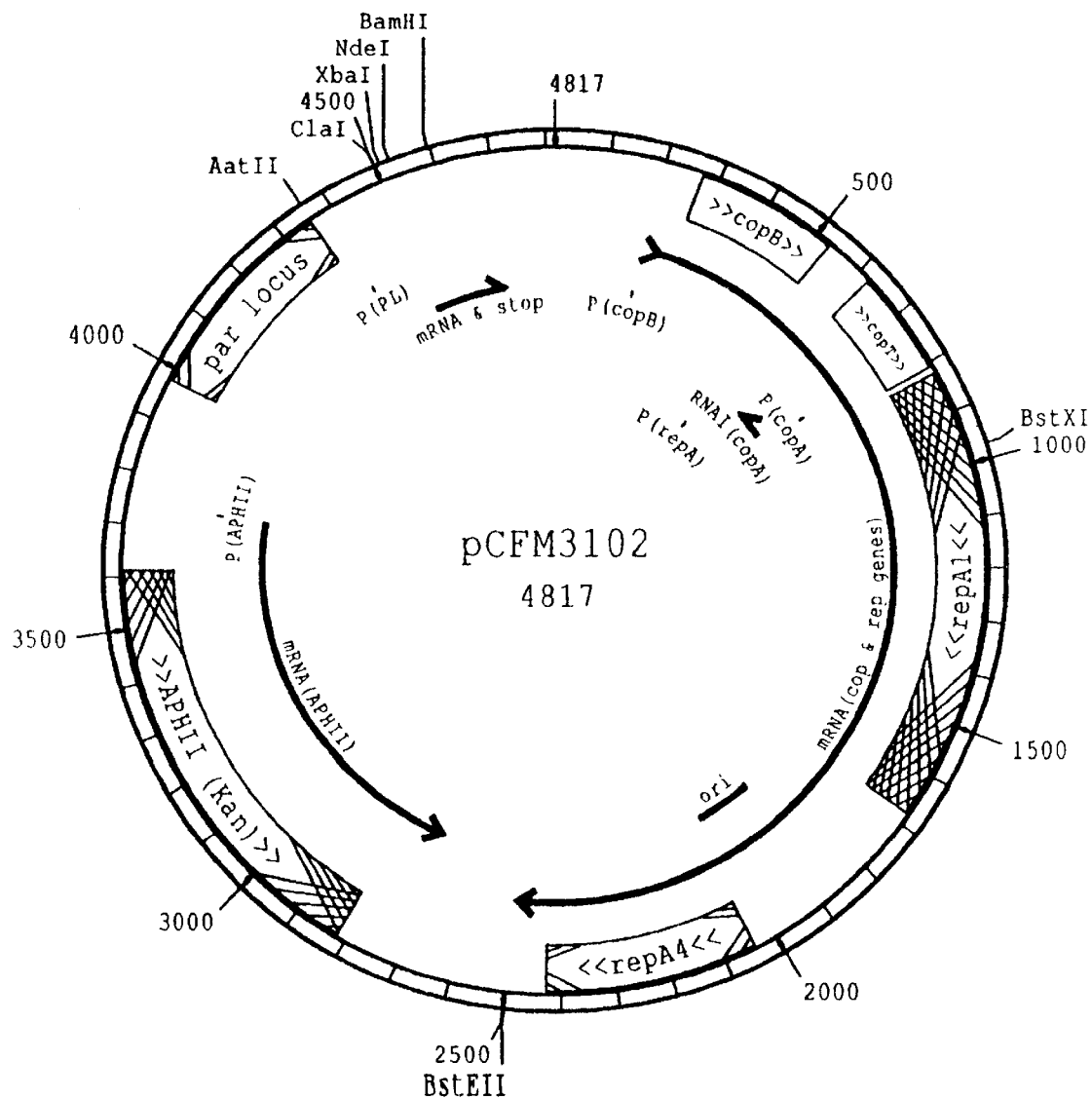

(ATCC 69702), pCFM1656 (ATCC 69576), and pCFM3102 (FIGS. 2A, 2B and 2C, respectively). The plasmid p3102 can be derived from the plasmid pCFM1656 by making a series of site directed base changes with PCR overlapping oligo mutagenesis. Starting with the BglII site (pCFM1656 plasmid bp #180) immediately 5' to the plasmid replication promoter, $P_{copB}$, and proceeding toward the plasmid replication genes, the base pair changes are as follows:

| pCFM1656 bp # | bp in pCFM1656 | bp changed to in pCFM3102 |
| --- | --- | --- |
| #204 | T/A | C/G |
| #428 | A/T | G/C |
| #509 | G/C | A/T |
| #617 | — — | insert two G/C bp |
| #677 | G/C | T/A |
| #978 | T/A | C/G |
| #992 | G/C | A/T |
| #1002 | A/T | C/G |
| #1005 | C/G | T/A |
| #1026 | A/T | T/A |
| #1045 | C/G | T/A |
| #1176 | G/C | T/A |
| #1464 | G/C | T/A |
| #2026 | G/C | bp deletion |
| #2186 | C/G | T/A |
| #2479 | A/T | T/A |
| #2498-2501 | AGTG TCAC | GTCA CAGT |
| #2641-2647 | TCCGAGC AGGCTCG | bp deletion |
| #3441 | G/C | A/T |
| #3452 | G/C | A/T |
| #3649 | A/T | T/A |
| #4556 | — | insert bps |

(SEQ ID NO:43) 5'-GAGCTCACTAGTGTCGACCTGCAG-3'
(SEQ ID NO:44) 5'-CTCGAGTGATCACAGCTGGACGTC-3'

As seen above, pCFM1156, pCFM1656 and pCFM3102 are very similar to each other and contain many of the same restriction sites. The plasmids were chosen by convenience, and the vector DNA components can be easily exchanged for purposes of new constructs. The host used for all cloning was E. coli strain FM5 (ATCC: 53911) and the transformations were carried out (according to the method of Hanahan (1983), supra) or by electroelution with a Gene Pulser™ transfection apparatus (BioRad Laboratories, Inc., Hercules, Calif.), according to the manufacturer's protocol.

Initially, a small, freshly-cultured inoculum of the desired recombinant E. coli clone harboring the desired construct on one of the three pCFM vectors was started by transferring 0.1 mL of a frozen glycerol stock of the appropriate strain into a 2 L flask containing 500 mL of Luria broth. The culture was shaken at 30° C. for 16 hours. Thereafter the culture was transferred to a 15 L fermentor containing 8 L of sterile batch medium (Tsai, et al. (1987), J. Industrial Microbiol., 2:181–187.)

Feed batch fermentation starts with the feeding of Feed # 1 medium (Tsai, et al. (1987.), supra). When the OD600 reached 35, expression of the desired KGF analog was induced by rapidly raising the culture temperature to 37° C. to allow the amplification of plasmid. After two hours at 37° C., the culture temperature was quickly raised to 42° C. to denature the CI repressor and the addition of Feed 1 was discontinued in favor of Feed 2, the addition rate of which was initiated at 300 mL/hr. Feed 2 comprised 175 g/L trypticase-peptone, 87.5 g/L yeast extract, and 260 g/L glucose. After one hour at 42° C., the culture temperature was decreased to 36° C., where this temperature was then maintained for another 6 hours.

The fermentation was then halted and the cells were harvested by centrifugation into plastic bags placed within 1 L centrifuge bottles. The cells were pelleted by centrifugation at 400 rpm for 60 minutes, after which the supernatants were removed and the cell paste frozen at −90° C.

Following expression of the various KGF analogs in E. coli, native KGF, C(1,15)S, R(144)Q, C(1,15)S/R(144)Q, ΔN15, ΔN23, and ΔN23/R(144)Q protein were purified using the following procedure. Cell paste from a high cell density fermentation was suspended at 4° C. in 0.2 M NaCl, 20 mM NaPO$_4$, pH 7.5 as a 10–20% solution (weight per volume) using a suitable high shear mixer. The suspended cells were then lysed by passing the solution through a homogenizer (APV Gaulin, Inc., Everett, Mass.) three times. The outflowing homogenate was cooled to 4–8° C. by using a suitable heat exchanger. Debris was then removed by centrifuging the lysate in a J-6B™ centrifuge (Beckman Instruments, Inc., Brea, Calif.) equipped with a JS 4.2 rotor at 4,200 rpm for 30–60 min. at 4° C. Supernatants were then carefully decanted and loaded onto a previously prepared 450 mL (5 cm×23 cm) column of S-Sepharose Fast Flow™ resin (Pharmacia) column equilibrated with 0.2 M NaCl, 20 mM NaPO$_4$, pH 7.5 at 4° C. Next, the column was washed with five column volumes (2250 mL) of 0.4 M NaCl, 20 mM NaPO$_4$, pH 7.5 at 4° C. The desired protein was eluted by washing the column with 5 L of 0.5 M NaCl, 20 mM NaPO$_4$, pH 7.5. Again, 50 mL fractions were collected and the A$_{280}$ of the effluent was continuously monitored. Fractions identified by A$_{280}$ as containing eluted material were then analyzed by SDS-PAGE through 14% gels to confirm the presence of the desired polypeptide.

Those fractions containing proteins of interest were then pooled, followed by the addition of an equal volume of distilled water. The diluted sample was then loaded onto a previously prepared 450 mL (5 cm×23 cm) column of S-Sepharose Fast Flow equilibrated with 0.4 M NaCl, 20 mM NaPO$_4$, pH 6.8 at 4° C. The column was washed with 2250 mL of 0.4 M NaCl, 20 mM NaPO$_4$, pH 6.8 and the protein eluted using a 20 column volume linear gradient ranging from 0.4 M NaCl, 20 mM NaPO$_4$, pH 6.8 to 0.6 M NaCl, 20 mM NaPO$_4$, pH 6.8. Again, 50 mL fractions were collected under constant A$_{280}$ monitoring of the effluent. Those fractions containing the protein (determined by 14% SDS-PAGE) were then pooled, followed by concentration through a YM-10 membrane (10,000 molecular weight cutoff) in a 350cc stirring cell (Amicon, Inc. Mayberry, Mass.) to a volume of 30–40 mL.

The concentrate was then loaded onto a previously generated 1,300 mL (4.4 cm×85 cm) column of Superdex-75™ resin (Pharmacia) equilibrated in column buffer comprising 1X PBS (Dulbecco's Phosphate Buffered Saline, "D-PBS," calcium and magnesium-free) or 0.15 M NaCl, 20 mM NaPO$_4$, pH 7.0. After allowing the sample to run into the column, the protein was eluted from the gel filtration matrix using column buffer. Thereafter, 10 mL fractions were recovered and those containing the analog (determined by 14% SDS-PAGE) were pooled. Typically, the protein concentration was about 5-10 mg/mL in the resultant pool. All of the above procedures were performed at 4–8° C., unless otherwise specified.

An alternative purification procedure was used to purify native KGF, C(1,15)S and ΔN23. The procedure involves the following steps and, unless otherwise specified, all procedures, solutions and materials were conducted at 23±5° C.

Upon completion of the production phase of a bacterial fermentation, the cell culture was cooled to 4–8° C. and the cells were harvested by centrifugation or a similar process.

On the basis of the expected yield of protein per unit weight of cell paste and the amount of purified protein required, an appropriate amount of cell paste, by weight, was suspended in a mild buffer solution, 20 mM NaPO$_4$, 0.2 M NaCl, pH 7.5, weighing about five times that of the cell paste to be suspended. The cells were dispersed to a homogeneous solution using a high shear mixer. The temperature of the cell paste dispersion was maintained at 4–8° C. during homogenization.

The cells were then lysed by pressure, for example by passing the cell paste dispersion twice through an appropriately sized cell homogenizer. The homogenate was kept chilled at 5±3° C. To clarify the cell lysate, a previously prepared depth filter housing (Cuno, Inc., Meriden, Conn.) equipped with a filter having an appropriate amount of filter surface area, equilibrated with a suitable volume of 0.2 M NaCl, 20 mM NaPO$_4$, pH 7.5 was employed. The equilibration and clarification were performed at 5±3° C. Prior to clarification, an appropriate amount of a suitable filter aid was used to pre-coat the filter and be thoroughly mixed with the cell lysate, after which the lysate was clarified by passing the solution through the filter apparatus. The filter was washed with 0.2 M NaCl, 20 mM NaPO4, pH 7.5. The filtrate and any subsequent wash were collected in a chilled container of suitable capacity, all the while being maintained at less than 10° C.

Following clarification the lysate was then passed through a previously prepared column of SP-Sepharose Fast Flow containing at least 1 mL of resin per 2 g of cell paste. The column of SP-Sepharose Fast Flow was equilibrated with cold (5±3° C.), 0.2 M NaCl, 20 mM NaPO$_4$, pH 7.5. The temperature of the column was maintained at less than 10° C. The clarified lysate (5±3° C.) was then loaded onto the ion exchange column, with the absorbance at 280 nm ($A_{280}$) of eluate being continuously monitored. After sample loading, the column was washed with cold 0.2 M NaCl, 20 mM NaPO$_4$, pH 7.5, followed by washing with 0.3 M NaCl, 20 mM NaPO$_4$, pH 7.5 at 23±5° C.

To elute the desired protein, a linear gradient ranging from 0.2–1 M NaCl, 20 mM NaPO$_4$, pH 7.5 was used. Bulk product was collected in several fractions on the basis of the $A_{280}$ of the eluate. Following elution, these fractions were pooled and the volume noted.

To oxidize free sulfhydryl groups, an oxidation step was performed. For proteins with altered cysteine patterns, as compared to native KGF, an oxidizing agent (e.g., cystamine dihydrochloride or another appropriate oxidizing agent, for instance, cystine, oxidized glutathione or divalent copper) was added to a final concentration of 1–20 mM and the pH was adjusted to 7–9.5, with a pH of 9.0±0.3 when cystamine dihydrochloride was used. The oxidation was conducted at 10–30° C. for an appropriate period. For the native KGF protein, oxidation was accomplished by adding an appropriate amount of (NH$_4$)$_2$SO$_4$ such as 1–2 M (NH$_4$)$_2$SO$_4$, adjusting the pH to 7.5–9.5, and holding the temperature at 23±5° C. for an appropriate period.

After oxidation, the pH of the solution was adjusted to between 6.5 and 9.5. If necessary, solid (NH$_4$)$_2$SO$_4$ was added to the solution to a final concentration of 2 M. To remove particulates, the solution was passed through appropriate clarification filters.

The filtered, oxidized product was then subjected to hydrophobic interaction chromatography (HIC). The HIC matrice was Butyl-650M Toyopearl™ resin (Tosohaas, Inc., Montgomeryville, Pa.). The protein-containing solution was loaded onto the column, which had been previously equilibrated with 2 M (NH$_4$)$_2$SO$_4$, 0.15 M NaCl, 20 mM NaPO$_4$, pH 7.0. After sample loading, the column was washed with 2 M (NH$_4$)$_2$SO$_4$, 0.15 M NaCl, 20 mM NaPO$_4$, pH 7.0. The desired protein was then eluted using a decreasing linear (NH$_4$)$_2$SO$_4$ gradient ranging from 2–0 M developed in 0.15 M NaCl, 20 mM NaPO4, pH 7.0. When the desired protein began to elute, as indicated by an increase in the $A_{280}$ of the eluate, fractions were collected. Aliquots of each fraction were then analyzed by SDS-PAGE. Those fractions containing the desired protein were then pooled, thoroughly mixed, and the volume of the pool determined, as was the concentration of the protein therein.

The pooled HIC protein-containing eluate was then concentrated and the elution buffer exchanged. Typically, proteins were concentrated to 5.0–10.0 mg/mL. Ultrafiltration was conducted using an ultrafiltration system equipped with a Pellicon™ cassette system (Millipore, Inc., Bedford, Mass.) with an appropriately sized cut-off membrane After concentration, the sample was diafiltered against an appropriate buffer. The retentate from the concentration step was diafiltered against 0.15 M NaCl, 20 mM NaPO$_4$, pH 7.0 until the conductivity of the retentate was within 5% of the conductivity of the 0.15 M NaCl, 20 mM NaPO$_4$, pH 7.0 solution.

In addition, to remove precipitates and bacterial endotoxin that might be present, the concentrated diafiltered protein-containing sample was passed through a 0.1 µm Posidyne™ filter (Pall, Inc., Cortland, N.Y.). After determining the protein concentration of the solution and on the basis of the desired concentration of the final bulk product, the solution was diluted with 0.15 M NaCl, 20 mM sodium phosphate, pH 7.0, to the desired final concentration. A final aseptic filtration through a 0.22 µm filter, was then performed as the final bulk product was transferred to a pyrogen-free container for storage (at about 5° C.) for further formulation.

EXAMPLE 3

Purification from Mammalian Cell Culture

This example describes the expression, isolation, and characterization of two biologically active recombinant KGF (rKGF) forms produced in a mammalian expression system.

The human KGF gene was isolated by PCR amplification of cDNA made from normal dermal human fibroblast cells (Clonetec, Inc., Palo Alto, Calif.). Following the making of cDNA by reverse transcriptase, PCR was used to amplify the KGF gene. OLIGO#25 and OLIGO#26 were used to amplify the gene out of the cDNA and OLIGO#27 and OLIGO#28 were used to place HindIII and BglII restriction sites at the fragment ends by a second PCR amplification, as set forth in FIG. 1.

OLIGO#25 (SEQ ID NO:45):
  5'-CAATCTACAATTCACAGA-3'
OLIGO#26 (SEQ ID NO:46):
  5'-TTAAGTTATTGCCATAGG-3'
OLIGO#27 (SEQ ID NO:47):
  5'-AACAAAGCTTCTACAATTCACAGATAGGA-3'
OLIGO#28 (SEQ ID NO:48):
  5'-AACAAGATCTTAAGTTATTGCCATAGG-3'

Following cloning and DNA sequence confirmation, the KGF gene DNA was then used. Amplification was effected using two primers:

OLIGO#29 (SEQ. ID. NO:49):
  5'-CGGTCTAGACCACCATGCACAAATGGATACTGACATGG-3

OLIGO#30 (SEQ. ID. NO:50): 5'-GCCGTCGACCTA TTAAGTTATTGCCATAGGAAG-3'

The sense primer, OLIGO#29, included an XbaI site and a consensus Kozak translation sequence (5'-CCACC-3') upstream of the start codon, ATG. The antisense primer, OLIGO#30, included a SalI cloning site and an additional stop codon. After 18 cycles of PCR amplification (30 sec. denaturation at 94° C., 40 sec. annealing at 55° C., and 40 sec. elongation at 72° C.), the product was digested with XbaI and SalI and ligated with a similarly digested DNA of pDSRα2 (according to the methods of Bourdrel et al. (1993), *Protein Exp. & Purif.*, 4:130–140 and Lu et al. (1992), *Arch. Biochem. Biophys.*, 298:150–158). This resulted in plasmid KGF/pDSRΔ2 which placed the human KGF gene between the SV40 early promoter and the α-FSH polyadenylation sequences. Two clones were picked and DNA sequence analysis confirmed construction of the desired vector.

Two micrograms of KGF/pDSRΔ2 DNA were then linearized with PvuI. Chinese hamster ovary (CHO) cells, seeded the day before at $0.8 \times 10^6$ cells/60 mm culture dish, were then transfected with the treated DNA using a standard calcium phosphate precipitation method (Bourdrel et al., supra). Two weeks later, individual colonies were picked and transferred into 24-well plates. The conditioned media was considered serum-free when the cells reached confluency and aliquots thereof were analyzed by Western blotting using a polyclonal rabbit antiserum reactive against *E. coli*-expressed human KGF.

Westerns were performed by running samples through 12.5% (w/v) SDS polyacrylamide gels, followed by electroblotting for 1 hr. at 400 mA onto nitrocellulose membranes using a semidry transfer apparatus (Hoefer Scientific Instruments, San Francisco, Calif.). 20 mM Tris, 150 mM glycine, 20% methanol served as the transfer buffer. The nitrocellulose sheets were blocked by incubation with 10% normal goat serum in PBS. Rabbit anti-serum raised against *E. coli*-derived KGF was used as primary antibody. For use, it was diluted 1/10,000 in 1% normal goat serum in PBS and incubated with the blocked nitrocellulose sheets for 12 hr. at room temperature, after which excess antibody was removed by three 30 min. washes in PBS. The nitrocellulose membranes were then incubated in 100 mL of 1% normal goat serum in PBS containing Vectastain™ biotinylated goat anti-rabbit IgG (secondary antibody, Vector Labs, Burlingame, Calif.), for 30 minutes at room temperature. After three 10 minute washes in PBS, a 30 minute room temperature incubation was performed in a 100 mL solution of 1% normal goat serum containing streptavidin and biotinylated peroxidase, prepared according to manufacturer's directions (Vector Labs). Following three washes in PBS, KGF cross-reactive material was visualized by incubation in a mixture of 60 μL of 30% (w/v) $H_2O_2$ in 100 mL of PBS and 50 mg of 4-chloronapthol in 20 mL of methanol. The reaction was stopped by rinsing in water after 10 minutes.

Analysis of the blots revealed that the KGF-specific antibody associated with three distinct protein bands, two being closely related with molecular weights of about 25–29 kDa and one with an estimated molecular weight of about 17 kDa, as compared to the expected molecular weight of approximately 18.8 of the 163 amino acid mature protein. Additionally, several high expressing clones secreting more than 2.0 mg of rKGF per liter, as judged by Western analysis, were selected and expanded into roller bottles (according to the method of Lu et al., supra) to generate large volumes of serum-free conditioned medium for purification of KGF by cationic exchange chromatography and gel filtration, as set forth below.

KGF from 3 L of serum-free conditioned medium was purified applying the medium directly to a cation exchange column (5×24 cm) packed with 450 mL of sulfoethyl column of SP-Sepharose Fast Flow(Pharmacia) pre-equilibrated with 20 mM sodium phosphate, pH 7.5. After washing with five column volumes of 20 mM sodium phosphate, 0.2 M NaCl, pH 7.5, rKGF was eluted using a 20 column volume linear gradient of 0.2 to 1.0 M NaCl in 20 mM sodium phosphate, pH 7.5. 50 mL fractions were collected with continuous $A_{280}$ monitoring. KGF protein was detected by analyzing aliquots of each fraction by SDS-PAGE. SDS-PAGE was performed on an electrophoresis system (Novex, San Diego, Calif.) using precast 14% Tris-glycine precast gels (according to the method of Laemmli (1970), *Nature*, 227:680–685). Samples were mixed with non-reducing SDS sample buffer without heating before loading. The proteins were detected by either Coomassie blue or silver staining. Two late-eluting peaks were seen to contain protein bands corresponding to the 25–29 kDa and 17 kDa bands detected by Western blot. The fractions containing each of these peaks were separately concentrated to a volume of less than 1.0 mL and subjected to gel filtration.

The gel filtrations employed columns of Superdex-75™ resin (HR 10/30, Pharmacia) pre-equilibrated with PBS, pH 7.2, and calibrated with the following known molecular weight standards (BioRad, San Francisco, Calif.): thyroglobulin (670 kDa), gamma globulin (158 kDa), ovalbumin (44 kDa), myoglobin (17 kDa) and vitamin B-12 (1.4 kDa). These purification steps resulted in an approximate 2000-fold purification of rKGF, specifically including a 17 kDa and a 30 kDa material, as estimated by silver staining.

In the instance of the higher molecular weight material, rKGF eluted as a major symmetrical peak, which was called KGF-a. Upon SDS-PAGE analysis of a lesser amount of this material, 3 μg/lane versus 6 μg/lane, two bands with a 1–2 kDa molecular weight difference were resolved. In the instance of the lower molecular weight material, termed KGF-b, gel filtration resulted in a protein preparation having the expected mobility. For both KGF-a and KGF-b, the overall yield after purification was approximately 30–40%.

Amino acid sequences from KGF-a and KGF-b were also analyzed. These analyses were performed on an automatic sequencer (Model 477A or 470A, Applied Biosystems, Inc., Foster City, Calif.) equipped with a Model 120A on-line PTH-amino acid analyzer and a Model 900A data collection system (according to the method of Lu et al. (1991), *J. Biol. Chem.*, 266:8102–8107). Edman sequence analysis of KGF-a revealed a major N-terminal sequence of $X_1$-N-D-M-T-P-E-Q-M-A-T-N-V-$X_2$-$X_3$-S- (SEQ ID NO:51). A minor sequence starting from the third N-terminal amino acid, aspartic acid, was also present in 1.6% of the total sequenceable protein. $X_1$, $X_2$, and $X_3$ were the unassigned due to the absence of phenylthiohydantoinyl (PTH) amino acid signals during sequence analysis.

Interestingly, N-terminal sequence analysis of KGF-b revealed an N-terminal amino acid sequence of S-Y-D-Y-M-E-G-G-D-I-R-V- (SEQ ID NO:52), indicating that it is an N-terminally truncated form of KGF that has been proteolytically cleaved at the $Arg^{23}$-$Ser^{24}$ peptide bond.

To further characterize purified KGF-a and KGF-b, the protein was subjected to glycosidases (neuraminidase, O-glycanase, and/or N-glycanase), using known techniques (Sasaki et al. (1987), *J. Biol. Chem.*, 262:12059–12076; Takeuchi et al. (1988), *J. Biol. Chem.*, 263:3657–3663; Zsebo et al. (1990), *Cell*, 63:195–201). These data indicate that KGF-a contains N- and O-linked carbohydrates, although the lower molecular weight form of KGF-a probably contains only N-linked sugar. Glycosidase treatment did not cause molecular weight reduction for KGF-b, indicating that the molecule is unglycosylated.

EXAMPLE 4

Biological Activity

Each KGF analog was diluted and assayed for biological activity by measuring the [$^3$H]-thymidine uptake of Balb/MK cells (according to the method of Rubin et al. (1989), supra). The samples were first diluted in a bioassay medium consisting of 50% customer-made Eagle's MEM, 50% customer-made F12, 5 μg/mL transferrin, 5 ng/mL sodium selenite, 0.0005% HSA and 0.005% Tween 20. KGF samples were then added into Falcon Primeria 96-well plates seeded with Balb/MK cells. Incorporation of [$^3$H]-Thymidine during DNA synthesis was measured and converted to input native KGF concentration by comparison to a native KGF standard curve. Each of the tested analogs exhibited mitogenic activity.

Interaction with the KGF receptor was examined using isolated KGF receptor membrane preparations prepared from Balb/MK mouse epidermal keratinocytes (by the procedure described by Massague (1983), *J. Biol. Chem.*, 258:13614–13620). Specifically, various forms of KGF were diluted with 50 mM Tris-HCl, pH 7.5, containing 0.2% bovine serum albumin so as to range in concentration from 0.8 ng to 100 ng per 50 μL. They were individually incubated with the membrane preparation (75 ng/mL) and $^{125}$I-labeled *E. coli*-derived KGF (1.5 ng). Receptor binding and competition experiments were performed at 4° C. for 16 hr., after which time samples were taken, centrifuged, and washed twice with the above diluent buffer to remove unbound and non-specifically bound, labeled KGF. Samples were then counted for the remaining radioactivity. Competition curves for receptor binding between KGF samples and labeled KGF were constructed by plotting percent uncompetition versus concentrations of each KGF sample. Radioreceptor assay uncompetition experiments indicated that *E. coli*-derived KGF, KGF-a, and KGF-b have similar receptor binding activity.

While the present invention has been described above both generally and in terms of preferred embodiments, it is understood that other variations and modifications will occur to those skilled in the art in light of the description above.

What is claimed is:

1. A method for purifying a keratinocyte growth factor (KGF), the method comprising:
   a) obtaining a solution comprising the KGF;
   b) loading the KGF from the solution of part a) to a cation exchange resin;
   c) eluting the KGF in an eluate solution from the cation exchange resin;
   d) passing the KGF through an appropriate molecular weight exclusion matrix; and
   e) recovering the KGF from the molecular weight exclusion matrix,
   wherein said KGF is not purified by heparin affinity chromatography.

2. The method according to claim 1, wherein the KGF is produced in procaryotic cells.

3. The method according to claim 1, wherein the KGF is produced in *E. coli*.

4. The method according to claim 1, wherein the KGF is produced in mammalian cells.

5. The method according to claim 4, wherein the KGF is produced in Chinese hamster ovary cells.

6. The method according to claim 1, wherein the cation exchange resin is selected from the group consisting of carboxymethyl cellulose, carboxymethyl agarose and sulfated agarose and cellulose columns.

7. The method according to claim 1, wherein the molecular weight exclusion matrix is selected from the group consisting of agarose-based, acrylamide-based, silica-based or polymer-based size-exclusion columns.

8. The method according to claim 1, wherein said KGF comprises an amino acid sequence of mature keratinocyte growth factor (amino acid residues 32-194 of SEQ ID NO:2) or a mutein thereof selected from the group consisting of C(1,15)S, ΔN15, ΔN 16, ΔN17, ΔN18, ΔN19, ΔN20, ΔN21, ΔN22, ΔN23, ΔN24, ΔN3/C(15)S, ΔN3/C(15)-, ΔN8/C(15) S, ΔN8/C(15)-, C(15)S/R(144)E, C(1,15)S/R(144)Q, ΔN23/R(144)Q, C(1,15,40)S, C(1,15,102)S, C(1,15,102,106)S, ΔN23/N(137)E, ΔN23/K(139)E, ΔN23/K(139)Q, ΔN23/R(144)A, ΔN23/R(144)E, ΔN23/R(144)L, ΔN23/K(147)E, ΔN23/K(147)Q, ΔN23/K(153)E, ΔN23/K(153)Q, ΔN23/Q(152)E/K(153)E, R(144)Q and H(116)G, wherein the initial methionine is optional.

9. The method according to claim 8, wherein the KGF is selected from the group consisting of mature KGF, C(1,15) S, C(1,15)S/R(144)E, C(1,15)S/R(144)Q, ΔN15, ΔN23 and ΔN23/R(144)Q, wherein the initial methionine is optional.

10. A method for purifying a keratinocyte growth factor (KGF), the method comprising:
   a) obtaining a solution comprising the KGF;
   b) loading the KGF from the solution of part a) to a cation exchange resin;
   c) eluting the KGF in an eluate solution from the cation exchange resin;
   d) oxidizing, the KGF to form an oxidized KGF;
   e) passing the oxidized KGF through a hydrophobic interaction chromatography matrix; and
   f) recovering the KGF from the hydrophobic interaction chromatography step.

11. The method according to claim 10, wherein the KGF is produced in procaryotic cells.

12. The method according to claim 11, wherein the KGF is produced in *E. coli*.

13. A method according to claim 12, wherein the KGF is ΔN23 (with the initial methionine being optional) which is purified by a method comprising:
   a) obtaining a solution comprising ΔN23;
   b) loading ΔN23 from the solution of part a) to a cation exchange resin, wherein said cation exchange resin is selected from the group consisting of carboxymethyl cellulose, carboxymethyl agarose, sulfated agarose and cellulose columns;
   c) eluting ΔN23 in an eluate solution from the cation exchange resin;
   d) contacting ΔN23 with an oxidizing agent to form an oxidized ΔN23, wherein the oxidizing agent is selected from the group consisting of cystamine dihydrochloride, cystine, oxidized glutathione and divalent copper;
   e) passing the oxidized ΔN23 through a hydrophobic interaction chromatography matrix, wherein the hydrophobic interaction chromatography matrix is selected from a column having an alkyl- or phenyl-substituted resin; and
   f) recovering ΔN23 from the hydrophobic interaction chromatography step.

14. A method according to claim 12, wherein the KGF is ΔN16 (with the initial methionine being optional) which is purified by a method comprising:

a) obtaining a solution comprising ΔN16;

b) loading ΔN16 from the solution of part a) to a cation exchange resin, wherein said cation exchange resin is selected from the group consisting of carboxymethyl cellulose, carboxymethyl agarose, sulfated agarose and cellulose columns;

c) eluting ΔN16 in an eluate solution from the cation exchange resin;

d) contacting ΔN16 with an oxidizing agent to form an oxidized ΔN16, wherein the oxidizing agent is selected from the group consisting of cystamine dihydrochloride, cystine, oxidized glutathione and divalent copper;

e) passing the oxidized ΔN16 through a hydrophobic interaction chromatography matrix, wherein the hydrophobic interaction chromatography matrix is selected from a column having an alkyl- or phenyl-substituted resin; and f) recovering ΔN16 from the hydrophobic interaction chromatography step.

15. The method according to claim 10, wherein the KGF is produced in mammalian cells.

16. The method according to claim 15, wherein the KGF is produced in Chinese hamster ovary cells.

17. The method according to claim 10, wherein the cation exchange resin is selected from the group consisting of carboxymethyl cellulose, carboxymethyl agarose, sulfated agarose and cellulose columns.

18. The method according to claim 10, wherein the hydrophobic interaction chromatography matrix is selected from a column having an alkyl- or phenyl-substituted resin.

19. The method according to claim 10, wherein the KGF is oxidized by being contacted with an oxidizing agent.

20. The method according to claim 19, wherein said oxidizing agent is selected from the group consisting of cystamine dihydrochloride, cystine, oxidized glutathione and divalent copper.

21. The method according to claim 10, wherein said KGF comprises an amino acid sequence of mature keratinocyte growth factor (amino acid residues 32-194 of SEQ ID NO:2) or a mutein thereof selected from the group consisting of C(1,15)S, ΔN15, ΔN 16, ΔN17, ΔN18, ΔN19, ΔN20, ΔN21, ΔN22, ΔN23, ΔN24, ΔN3/C(15)S, ΔN3/C(15)-, ΔN8/C(15)S, ΔN8/C(15)-, C(15)S/R(144)E, C(1,15)S/R(144)Q, ΔN23/R(144)Q, C(1,15,40)S, C(1,15,102)S, C(1,15,102,106)S, ΔN23/N(137)E, ΔN23/K(139)E, ΔN23/K(139)Q, ΔN23/R(144)A, ΔN23/R(144)E, ΔN23/R(144)L, ΔN23/K(147)E, ΔN23/K(147)Q, ΔN23/K(153)E, ΔN23/K(153)Q, ΔN23/Q(152)E/K(153)E, R(144)Q and H(116)G, wherein the initial methionine is optional.

22. The method according to claim 10, wherein the KGF is selected from the group consisting of mature KGF, C(1,15)S, C(1,15)S/R(144)E, C(1,15)S/R(144)Q, ΔN15, ΔN23 and ΔN23/R(144)Q, wherein the initial methionine is optional.

23. A method for purifying a keratinocyte growth factor (KGF), the method comprising:

a) obtaining a solution comprising the KGF;

b) loading the KGF from the solution of part a) to a cation exchange resin, wherein said cation exchange resin is selected from the group consisting of carboxymethyl cellulose, carboxymethyl agarose, sulfated agarose and cellulose columns;

c) eluting the KGF in an eluate solution from the cation exchange resin;

d) passing the KGF through an appropriate molecular weight exclusion matrix; and e) recovering the KGF from the molecular weight exclusion matrix.

24. The method according to claim 23, wherein the KGF is produced in procaryotic cells.

25. The method according to claim 23, wherein the KGF is produced in *E. coli*.

26. The method according to claim 23, wherein the KGF is produced in mammalian cells.

27. The method according to claim 26, wherein the KGF is produced in Chinese hamster ovary cells.

28. The method according to claim 23, wherein the molecular weight exclusion matrix is selected from the group consisting of agarose-based, acrylamide-based, silica-based or polymer-based size-exclusion columns.

29. The method according to claim 23, wherein said KGF comprises an amino acid sequence of mature keratinocyte growth factor (amino acid residues 32-194 of SEQ ID NO:2) or a mutein thereof selected from the group consisting of C(1,15)S, ΔN15, ΔN 16, ΔN17, ΔN18, ΔN19, ΔN20, ΔN21, ΔN22, ΔN23, ΔN24, ΔN3/C(15)S, ΔN3/C(15)-, ΔN8/C(15)S, ΔN8/C(15)-, C(15)S/R(144)E, C(1,15)S/R(144)Q, ΔN23/R(144)Q, C(1,15,40)S, C(1,15,102)S, C(1,15,102,106)S, ΔN23/N(137)E, ΔN23/K(139)E, ΔN23/K(139)Q, ΔN23/R(144)A, ΔN23/R(144)E, ΔN23/R(144)L, ΔN23/K(147)E, ΔN23/K(147)Q, ΔN23/K(153)E, ΔN23/K(153)Q, ΔN23/Q(152)E/K(153)E, R(144)Q and H(116)G, wherein the initial methionine is optional.

30. The method according to claim 29, wherein the KGF is selected from the group consisting of mature KGF, C(1,15)S, C(1,15)S/R(144)E, C(1,15)S/R(144)Q, ΔN15, ΔN23 and ΔN23/R(144)Q, wherein the initial methionine is optional.

* * * * *